United States Patent [19]

Amen et al.

[11] Patent Number: 4,865,969
[45] Date of Patent: Sep. 12, 1989

[54] PRODUCTION OF MICROORGANISMS

[75] Inventors: Jean Amen, Versailles; Michel Cabau, Coublevie Vioron, both of France

[73] Assignee: Eurozyme S.A., Paris, France

[21] Appl. No.: 764,939

[22] Filed: Aug. 9, 1985

Related U.S. Application Data

[63] Continuation-in-part of Ser. No. 374,736, May 4, 1982, abandoned.

[30] Foreign Application Priority Data

May 8, 1981 [FR] France ............................. 81 09153

[51] Int. Cl.$^4$ .......................... C12Q 3/00; C12R 1/01; C12R 1/46
[52] U.S. Cl. ..................................... 435/3; 435/252.1; 435/253.4; 435/802
[58] Field of Search .................. 435/3, 243, 244, 253, 435/289, 311, 802, 813, 252.1, 252.9, 253.4

[56] References Cited

U.S. PATENT DOCUMENTS

| | | | |
|---|---|---|---|
| 2,822,319 | 2/1958 | Monod | 435/813 X |
| 3,186,917 | 6/1965 | Gerhardt et al. | 435/244 |
| 3,418,208 | 12/1968 | Coty . | |
| 3,472,765 | 10/1969 | Budd et al. | 210/607 |
| 3,822,187 | 7/1974 | Chaffaut et al. | 435/813 X |
| 3,911,140 | 10/1975 | Osborne et al. | 435/253 X |
| 4,167,450 | 9/1979 | Chesbro et al. | 435/3 |

FOREIGN PATENT DOCUMENTS

| | | | |
|---|---|---|---|
| 0065895 | 12/1982 | European Pat. Off. | 435/3 |
| 2238759 | 2/1975 | France . | |

OTHER PUBLICATIONS

Stieber et al, Journal of Dairy Science, vol. 63, (1980), pp. 722–730.
Pelczar et al, Microbiology, New York, McGraw–Hill, 1972, pp. 127–128.
*Chemical Engineers Handbook*, 5th edition, Perry et al (ed.), New York, McGraw–Hill, 1973, pp. 19–83.
Chemical Abstracts, vol. 88, u:11 of Mar. 13, 1978, p. 383; 88:72975m, "Dialysis Continuous Process for Ammonium Lactate Fermentation of Whey: Methematical Model and Computer Simulation" by C. A. Coulman et al.
Chemical Abstracts, vol. 88, u:11 of 3/13/78, p. 383; 72976n, Dialysis Continuous Process for Ammonium Lactate Fermentation of Whey: Experimental Tests, by R. W. Stiepher et al.
Chemical Abstracts, vol. 90, No. 23 of Jun. 4, 1979 ref: 184876c, p. 465 by R. W. Stieber et al, "Dialysis Continuous Process for Ammonium–Lactate Fermentation: Improved Mathematical Model and Use of Deproteinized Whey".
Journal of Dairy Science, vol. 63, No. 5, 1980, by R. W. Stieber et al., pp.722–730, "Production of Lactobacillus Cells by Dialysis Continuous Fermentation of Deproteinized Whey".

*Primary Examiner*—Robert J. Warden
*Assistant Examiner*—Randall E. Deck
*Attorney, Agent, or Firm*—Finnegan, Henderson, Farabow, Garrett & Dunner

[57] ABSTRACT

This invention relates to the production of the microorganisms. The operation is conducted in two stages. The first stage is conducted in the absence of ultrafiltration while the pH of the growth medium is maintained within the range of 6–7 by the addition of a neutralizing agent. Nutrient substratum and dilution water are added during the first stage to maintain the growth rate at a constant level, and the volume of growth medium is permitted to increase. When the amount of growth inhibiting agent produced in the fermentation reaches a predetermined maximum level, the second stage is initiated and the growth rate is maintained in a range of 0.10 to 0.50/hr, which is less than the growth rate in the first stage. By increasing the amount of dilution water the concentration of the growth inhibiting agent is maintained so as to achieve the desired moderate growth rate. The growth inhibiting agent is also continuously removed from the growth medium during the second stage and the volume of the growth medium is maintained substantially constant. The invention may be applied to the production of lactic bacteria, in particular for example in the cheese and wine making industries.

11 Claims, 5 Drawing Sheets

PRODUCTION OF MICROORGANISMS

This application is a continuation-in-part of application Ser. No. 374,736 filed May 4, 1982, now abandoned.

BACKGROUND OF THE INVENTION

The present invention relates to the production of microorganisms.

The production of microorganisms is performed within a growth medium incorporating nutrient substrata diluted in water. This growth medium is initially seeded with microorganisms, which thus develop within a quasi-closed environment, except for the supply of neutralizing agent (so-called "batch" culture). This kind of fermentation applied on an industrial scale offers the advantage of an uncomplicated nature at the cost of low efficiency, since restrictive factors apply, be it within the nutrient substratum itself or in the inhibiting agents generated by the microorganisms, the ever rising concentration of which inhibiting agents during fermentation has the result of reducing the growth rate of the microorganisms.

To eliminate his disadvantage, it has been proposed to provide a continuous fermentation, that is, to make provision for metered extraction from the growth medium simultaneously with a complementarily metered infeed of nutrient substratum, neutralizer and water. This procedure renders it possible to increase the production of microorganisms for a fermenter of given volumetric capacity, but this at the cost of a reduced microorganism concentration in the extracted material. This kind of fermentation (referred to as "feed batch"), which renders it possible to diminish the deleterious action of the inhibitors by keeping their concentration at a restricted level, nevertheless has the major disadvantage of requiring a fermenter of greatly over-dimensioned capacity, so that this solution has very rarely been adopted by the industry.

It has also been proposed to make use of dialysis membranes or diaphragms which, under certain conditions, render it possible to eliminate the inhibiting agents formed and thereby to raise the final concentrations of microorganisms in the growth medium. This solution has not been adopted by the industry because membranes of this nature are decidedly too weak mechanically, thermally and chemically; their operational control is chancy and complex, their mode of operation at variable volume is not very desirable, and the ponderal yield of microorganisms produced as compared to the amount of substratum fed into the medium remains low.

The ultrafiltration diaphragm technique rendered it possible to take a leap forward in the fermentation of biological products. A recycled flow from the said growth medium is forced through an ultrafiltration cell, which may be selected to permit extraction of the inhibiting agent or agents, whereas the microorganisms are kept within the flow recycled into the growth medium. However, a portion of the nutrient substrata is unavoidably withdrawn with these inhibiting agents. It is thus possible to raise the final concentration of microorganisms in the growth medium to two or three times that of the so-called "batch" process. However, despite its remarkable qualities, it has been observed that in this last process a very pronounced reduction occurred in the subsequent growth rate of the microorganisms after a high initial development.

It is a main object of the present invention to provide a process which increases the final concentration of microorganisms in a process of this nature, whilst retaining an acceptable ponderal yield relative to the consumption of nutrient substrata.

SUMMARY OF THE INVENTION

In accordance with the invention, this result is obtained in a process of the kind in which an ultrafiltration operation is performed on the growth medium for partial elimination of an inhibiting agent formed, this during at least a part of the development stage of the said microorganisms, and also of the kind in which a minimum growth rate of the microorganisms in the said growth medium is assured, which rate in a first initial development stage has a high value and in a following stage has a constant, more moderate value, by the combination of the following steps:

(a) throughout the production period, the infeed of neutralizing agent is controlled to keep the pH value of the growth medium at a rigorously constant level not exceeding 7.5;

(b) the input of substratum and water are controlled with respect to the input of neutralizing agent, by determining the concentration of inhibiting agent surviving the action of said neutralizing agent;

(c) the whole of these inputs is provided directly into the fermenter throughout the production stage;

(d) the moderate value of the growth rate lies between 0.10 and 0.50 per hour;

(e) the moderate growth rate stage is initiated upon measuring a critical concentration of the inhibiting agent within the growth medium, which corresponds to a maximum acceptable concentration for said moderate growth rate selected; and (f) at least the essential stage of the ultrafiltration operation is positively linked to maintaining a constant volume of the said growth medium, in which the whole of the microorganisms produced is present.

Each of these conditions contributes to the desired result: very precise metering of the inputs of substratum and water owing to the strictly constant level at which the pH value is maintained by a neutralizing agent. Since recourse is had to precise pH value maintenance, the course of the fermentation may very easily be controlled by knowing the concentration of inhibiting agent and, since there is a correlation between the concentration of inhibiting agent and the growth rate, it is thus very easily possible by this means and after an initial stage to provide a somewhat more moderate growth rate which may be maintained throughout the fermentation process, whilst the ultrafiltration capacity to be applied to maintain a constant volume is itself closely linked to the growth rate selected. As a matter of fact, it will be understood that a lower concentration of inhibiting agent corresponds to a slower growth rate and consequently to a greater ultrafiltration capacity. It is one of the advantages of the invention to propose growth rates for the second development stage which may amount to 0.10 to 0.50 per hour but which in advantageous manner are comprised between 0.15 and 0.45 per hour, and even more advantageously between 0.20 and 0.40 per hour. For particular applications, it even proved possible to establish that the optimum value of the more moderate growth rate lies between 0.30 and 0.35 per hour. As has been stated, to each growth rate selected and to each microorganism cultivated, corresponds a critical maximum value of the inhibiting agent concentration, and it is precisely when this critical maximum value is reached that the adaptations are undertaken for the following stage of development at a more moderate growth rate.

According to an essential feature of the application of the inventive process, the rates of flow of substratum and water are kept at constant proportions, as compared to the rate of flow of neutralizing agent, through the initial development stage at high growth rate, and at different proportions throughout the following stage of development at more moderate growth rate during which the relative rate of flow of water is raised. The lower the value selected for the maximum acceptable concentration of inhibiting agent, the higher the value of the input water flow rate. This procedure, which consists in establishing the supply flow rates as a constant and optimized operating interlinkage, results in a minimum expenditure of substratum and as perfect as possible an adaptation of the nutritional requirements of the microorganisms to the growth it is decided to impart to them. Although the adaptations of the initial stage to the following stage may appear to be of little importance, it would otherwise be impossible to accomplish the specified success regarding the ponderal microorganisms yield relative to the amount of substrate consumed.

In addition to the main object hereinabove set forth, the invention also has as an object the production of lactic bacteria, of the kind in which a previously seeded growth medium is supplied with nutrient substratum which advantageously comprises lactose and yeast extract, and with ammonia (or soda) forming a neutralizing agent, the whole diluted in water, and in which the said growth medium has performed on it an operation for partial elimination of ammonium (or sodium) lactate, and this during at least a part of the development stage of the said lactic bacteria, of the kind in which a growth rate of the bacteria of the said growth medium is assured which has a high value during an initial development stage and a more moderate constant value during a subsequent stage. In this application, the invention specifies the following operating steps:

(a) throughout the production period, the input of ammonia (or soda) is controlled to keep the pH value of the growth medium at a rigorously constant level between 6 and 7;

(b) the inputs of substratum and water are controlled with respect to the input of ammonia (or soda), being initially controlled by determining the ammonium (or sodium) lactate concentration resulting from the action of the ammonia (or soda) on the lactic acid formed during the degradation of lactose;

(c) the onset of the stage having a more moderate growth rate is determined by measuring a critical concentration within the growth medium of the ammonium (or sodium) lactate, the critical ammonium lactate concentration being between 19 g/liter for a growth rate of 0.50/hr and 54 g/liter for a growth rate of 0.10/hr;

(d) at least the essential stage of the ultrafiltration operation is positively linked with maintaining a constant volume of the said growth medium.

As has been observed, this is an adaptation of the process described in the foregoing to a production in accordance with the specific conditions intended solely for lactic bacteria. As before, the decisive factors are the preliminary determination of the growth rate of the second development stage (rendering it possible to obtain a complete fermentation within a given period of time), and a critical maximum concentration of ammonium (or sodium) lactate which differs from one bacterium to another and, moreover, corresponds to this growth rate. By running tests on a very large number of strains, it thus proved possible to establish that the critical ammonium lactate concentrations is between say 19 g/liter (growth rate 0.50/hr), and say 54 g/liter (growth rate 0.10/hr), and more commonly between 25 g/liter and 35 g/liter. An essential approach of the inventive process thus consists in preliminary determination of the critical concentration of inhibiting agent, combined with the growth rate adopted.

During the development stage having a more moderate growth rate, the lactose concentration in the growth medium is comprised between 50 g/liter for a growth rate of 0.10/hr and 18 g/liter for a growth rate of 0.50/hr, the yeast extract concentration is comprised between 8 g/liter for a growth rate of 0.01/hr and 18 g/liter for a growth rate of 0.50/hr, and the ammonia concentration is comprised between 0.50N for a growth rate of 0.10/hr and 0.18N for a growth rate of 0.50/hr.

BRIEF DESCRIPTION OF THE DRAWINGS

In order that the invention may be more clearly understood, reference will now be made to the accompanying drawings, in which.

DETAILED DESCRIPTION OF PREFERRED EMBODIMENTS

Figure 1:
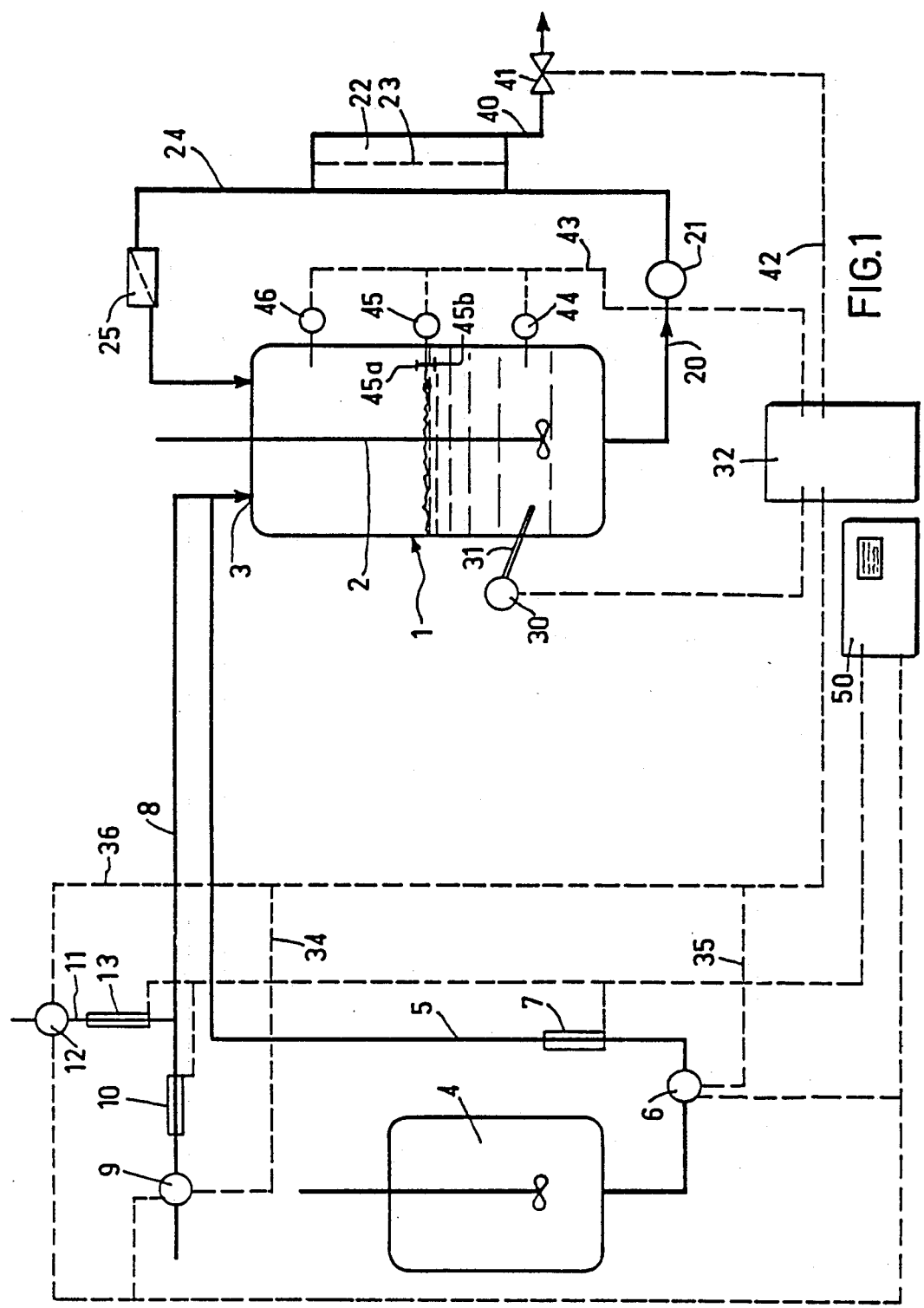
FIG. 1 is a diagrammatic view of one embodiment of apparatus for the production of lactic bacteria in accordance with the invention.

Referring now to FIG. 1, a fermenter 1 provided with stirring means 2 is supplied at its upper end 3 firstly with nutrient substratum (lactose and yeast) coming from a tank 4 by means of a pipe 5 provided with a pump 6 and with a summating flow meter 7, secondly with neutralizing ammonia via a pipe 8 provided with a pump 9 and with a summating flow meter 10, and thirdly with sterile water via a pipe 11 provided with a pump 12 and with a summating flow meter 13. The fermenter is also provided with an extraction pipe 20, incorporating a pump 21, leading to an ultrafiltration cell 22 comprising a diaphragm 23. The outlet at the upflow side of the diaphragm 23 of the ultrafiltration cell 22 is joined to the fermenter 1 via a pipe 24 incorporating a heat exchanger 25. A pH measuring device 30 having a sensor 31 engaged in a low portion of the fermenter 1 transmits a pH mensuration signal to a regulator 32. Based on this signal, the regulator 32 essentially makes provision via a control line 34 for appropriate control of the delivery of the ammonia pump 9, or of its operating period, in such manner that the pH value is kept at a constant level set in predetermined manner and which may be controlled as a function of the kind of bacteria being produced. The regulator 32 also acts via a control line 35 on the delivery or operating period of the substratum pump 6 and via a control line 36 on the delivery or operating period of the dilution water pump 12.

In conventional manner, the ultrafiltration cell 22 has a filtrate side outlet connected to the discharge via a pipe 40 incorporating a control valve 41 which for its part is positively coupled via a control line 42 to the regulator 32 which for this purpose receives data via a measurement line 43, from gauges indicating the minimum level 44, medium level 45 and maximum level 46. The medium level indicator 45 comprises two separate sensors 45a, 45b, in such manner that it may assure maintaining a constant level as will hereinafter be specified.

The operation of the apparatus which has just been described is as follows:

At the start of an operation for the production of microorganisms, a volume of substratum is fed into the fermenter 1 in such manner that the same reaches approximately the level of the level indicator 45. This growth medium is seeded with a lactic bacterium, a temperature of the order of 30° C. of the growth medium is assured by appropriate means, a nitrogen atmosphere is maintained above the growth medium at 0.5 bar; and the stirring means 2 is operated. Nutrient substratum, which within the tank 4 essentially comprises lactose at a concentration ($L_o$) and yeast at a concentration ($E_o$), is fed by the pump 6 into the pipe 5 at a rate of flow ($D_1$) (summation $T_1$), whereas ammonia at a concentration ($N_o$) is fed into the pipe 8 at a rate of flow ($D_2$) (summation $T_2$), whereas sterile water is fed into the pipe 11 at a rate of flow ($D_3$) (summation $T_3$).

During this first stage, the substratum concentration in the fermenter has been selected at a comparatively high value (lactose 45 g/liter, yeast extract 15 g/liter) on the one hand, and during a first initial development stage, the concentrations of lactose ($L_1$), yeast ($E_1$) and ammonia ($N_1$) penetrating into the fermenter 1 at the upper end (3), are maintained for example, at 40 g/liter for ($L_1$), 13.3 g/liter for ($E_1$) and 12N for ($N_1$). It will be noted that these concentrations may easily be determined from a control board (50) which receives the readings of the summating flow meters 7, 10 and 13.

Throughout this operating stage, it is of importance for satisfactory progression of the process, to check regularly on the growth rate, which should be at a maximum, this maximum rate typically being in a range between 0.70 and 0.80/hr.

This growth rate has an exponential stage applicable throughout the production process and is represented by the logarithmic growth constant of the biological mass as a function of time, according to the known formula $X = X_o e^{\mu t}$ (in which $\mu$ is the growth rate). Moreover, it is demonstrable that in the case of the sample selected the ammonium lactate formed by combining lactic acid (resulting from the consumption of lactose) and the ammonia fed in, is linked to the growth rate by the relationship $Lg_n dL/dt = \mu t + \text{const.}$, and it is observed that since determination of the ammonium lactate concentration is directly proportional to the intake of ammonia in a growth medium at constant pHO, it is sufficient to note the variation of the ammonia flow to determine the growth rate as a function of time: $\mu - Lg\, dL/dt\, /t$.

Consequently, it will be understood that the possible variation of the growth rate illustrated by the slope of the graph traced may be established at any instant and if applicable by means of the graph $Lg_n dL/dt = \mu_t + \text{const.}$, and that by means of appropriate corrections, it is possible on the contrary to keep this growth rate constant at a value preset by corrective adjustment of the supplies of substratum and water as compared to the neutralizer.

Throughout a first operating stage, the pump 21 of the ultrafiltration circuit is out of action and the level of the growth medium rises gradually from the level given by the indicator 45 to the level given by the indicator 46 (maximum volume). It is only when this level 46 is reached that the regulator 32 operates the controlled opening of the valve 41 via the control line 42, which allows the ultrafiltrate to be discharged and actually initiates the ultrafiltration operation.

Thus, in a manner known per se, the inhibiting agents such as ammonium lactate, are eliminated via the ultrafiltration diaphragm 23, whereas the lactic bacteria, on the other hand, are recycled to the fermenter 1 via the pipe 24. The level of the growth medium is reduced quickly until it reaches the intermediate level verified by the indicator 45. Once this level is reached, the regulator 32 is so programmed that the valve 41 shuts a little in such manner as to provide an almost constant level due to the two intermediate level sensors 45a and 45b which are positioned slightly spaced from each other.

A check on the operations is assured throughout this period, in particular on the growth rate which, as observed, is determined by the chronological logarithmic variations of the concentration of the ammonium lactate in the fermenter. Once an initially predetermined maximum lactate concentration is reached, which corresponds to a given growth rate for the bacteria grown, the operation is conducted in such manner that this ammonium lactate concentration is kept constant, which consequently has the effect that the bacteria growth rate is kept constant. To this end, as soon as this maximum ammonium lactate concentration value is reached, the supply of water provided by the pump 12 is increased such that the growth medium is diluted by a dilution factor F which is of the order of about 1.4 to 2, and in such manner as to feed quantities of ammonia into the fermenter which quantities correspond very precisely to keeping this maximum ammonium lactate concentration constant. The delivery ($D_3$) of the pump 12 may easily be determined so that the ammonia concentration fed in is that which corresponds to the concentration within the fermenter of ammonium lactate, thus assuring its retention.

It is thus possible to be certain of keeping the growth rate at a strictly constant level, by a slight complementary increase, usually of the order of 3 to 10% by weight, of the supply of substratum—whilst keeping the pH constant and in order to maintain constant the residual substratum concentration ($S_2$) and the lactate concentration ($I_2$) in the fermenter. Such an increase of the substratum supply is determined by the following rules where the primed letters indicate the corresponding concentrations and flows after this slight complementary increase and:

$S_1$ and $S'_1$ are the substratum concentrations at the input 3 of the fermenter with a rate $D_1$ ($D'_1$)

$N_1$ and $N'_1$ are the ammonia concentrations at the input of the fermenter with a rate $D_2$ ($D'_2$), where $D_2 = D'_2$ respectively during the initial and subsequent stages. To a lactate concentration ($I_2$) corresponds an ammonia concentration $N'_1$ with $$\frac{N_1}{N_1'} = F$$

so that $$S_1' = \frac{1}{F}(S_1 - S_2) + S_2$$

and

-continued
$$D_1' = \frac{(S_1')(D_2)(N_o)}{(S_o)(N_1')}$$

$$D_3' = \frac{(D_2)(N_o)}{N_1'} - (D_2' + D_1')$$

$N_o$ and $S_o$ being the concentrations of ammonia and substrate in stockages, respectively.

From the above formula:

$$\frac{D_1'}{D_1} = \left(\left(\frac{S_1 - S_2}{F}\right) + S_2\right)\left(\frac{F}{S_o}\right)\left(\frac{N_o}{N_1}\right)\left(\frac{D_2}{D_1}\right)$$

Examples with $S_2$ about $0.1\ S_1$

Example 1: $F = 1.4$;

$$\frac{D_1'}{D_1} = 1.040 \left(\frac{S_1}{S_o}\right)\left(\frac{N_o}{N_1}\right)\left(\frac{D_2}{D_1}\right)$$

Example 2: $F = 2$;

$$\frac{D_1'}{D_1} = 1.1 \left(\frac{S_1}{S_o}\right)\left(\frac{N_o}{N_1}\right)\left(\frac{D_2}{D_1}\right)$$

Numerical Example
$S_1 = 35$ g/l
$N_1 = 0.37$N
$D_1 = 159$ l/H
$D_2 = 35$ l/H
$D_3(H_2O) = 941$ l/H
$N_o = 12$N
$S_o = 250$ g/l
at the end of the initial stage (or beginning of the subsequent stage):
$S_2 = 4$ g/l
$I_2 = 28$ g/l
adjustments made at this time:
$F = 1.42$
$D'_1 = 168$ l/H (increase 6%)
$D'_2 = D_2$
$D'_3 = 1412$ l/H (increase 50%)

It should be noted that the operation of the ultrafiltration stage is positively linked to the growth medium reaching the level denoted by the level indicator 46, so that the implementation of ultrafiltration may, depending on circumstances, precede or follow the modification of the supply conditions deriving from setting the growth rate of the lactic bacteria at a more moderate level.

By way of example of the application of the inventive process, the critical ammonium lactate concentrations are given below for particular lactic bacteria, with specification of origin:

CNRZ: bacteria available from "Centre National de Recherches de Zootechniques" of Jouy-en-Josas, France;

NCDO: bacteria available from "National Collection of Dairy Organisms": of Reading (U.K.), and:
(SL) denoting "streptococcus lactis"
(SC$_r$) denoting "streptococcus cremoris"
(SD) denoting "streptococcus diacetyl lactis"

| Bacteria Types | Critical Concentration ($\mu = 0.35$/hr) (ammonium lactate) |
| --- | --- |
| CNRZ 269 (SL) | 30 g/liter |
| NCDO 763 (SL) | 26 g/liter |
| CNRZ 29 (SL) | 38 g/liter |
| NCDO 505 (SL) | 38 g/liter |
| NCDO 1198 (SL) | 26 g/liter |
| CNRZ 116 (SC$_r$) | 23 g/liter |
| NCDO 1009 (SC$_r$) | 21 g/liter |
| NCDO 699 (SC$_r$) | 26 g/liter |
| CNRZ 253 (SC$_r$) | 30 g/liter |
| NCDO 1000 (SC$_r$) | 21 g/liter |
| NCDO 1119 (SC$_r$) | 28 g/liter |
| NCDO 495 (SC$_r$) | 38 g/liter |
| CNRZ 124 (SD) | 28 g/liter |
| CNRZ 125 (SD) | 32 g/liter |

As a rule, the operation was begun with the substrata in the tank 4 at the highest possible concentrations, of the order of:
($L_o$) = 240 g/liter (lactose)
($E_o$) = 80 g/liter (yeast extract), and ammonia
($N_o$) = 12N (normality). The concentrations of the products entering the fermenter 1 may be determined at any instant; but equally and above all the momentary lactate concentration is defined by the relationship:

$$[\text{lactate}] = \frac{(T_2)(N_o)(107.11)}{V_o + T_1 + T_2 + T_3}$$

in which:
$T_1$ = summated substratum volume
$T_2$ = summated ammonia volume
$T_3$ = summated water volume
$V_o$ = initial volume in the fermenter
107.11 = molecular weight of ammonium lactate,
and the transition from the initial precursor stage operating at a high growth rate to the second stage having a more moderate growth rate, is performed simply by increasing the water delivery $D_3$, in such a manner as to match the concentration of ammonia fed into the ammonium lactate concentration in the fermenter, implying the following mathematical determination:

$$D_3 = \frac{(N_o)(107.11)(D_2)}{[\text{lactate}]} - (D_1 + D_2)$$

and if applicable at this instant, the supply of substratum is varied somewhat depending on attenuation of the growth rate.

Figure 2:
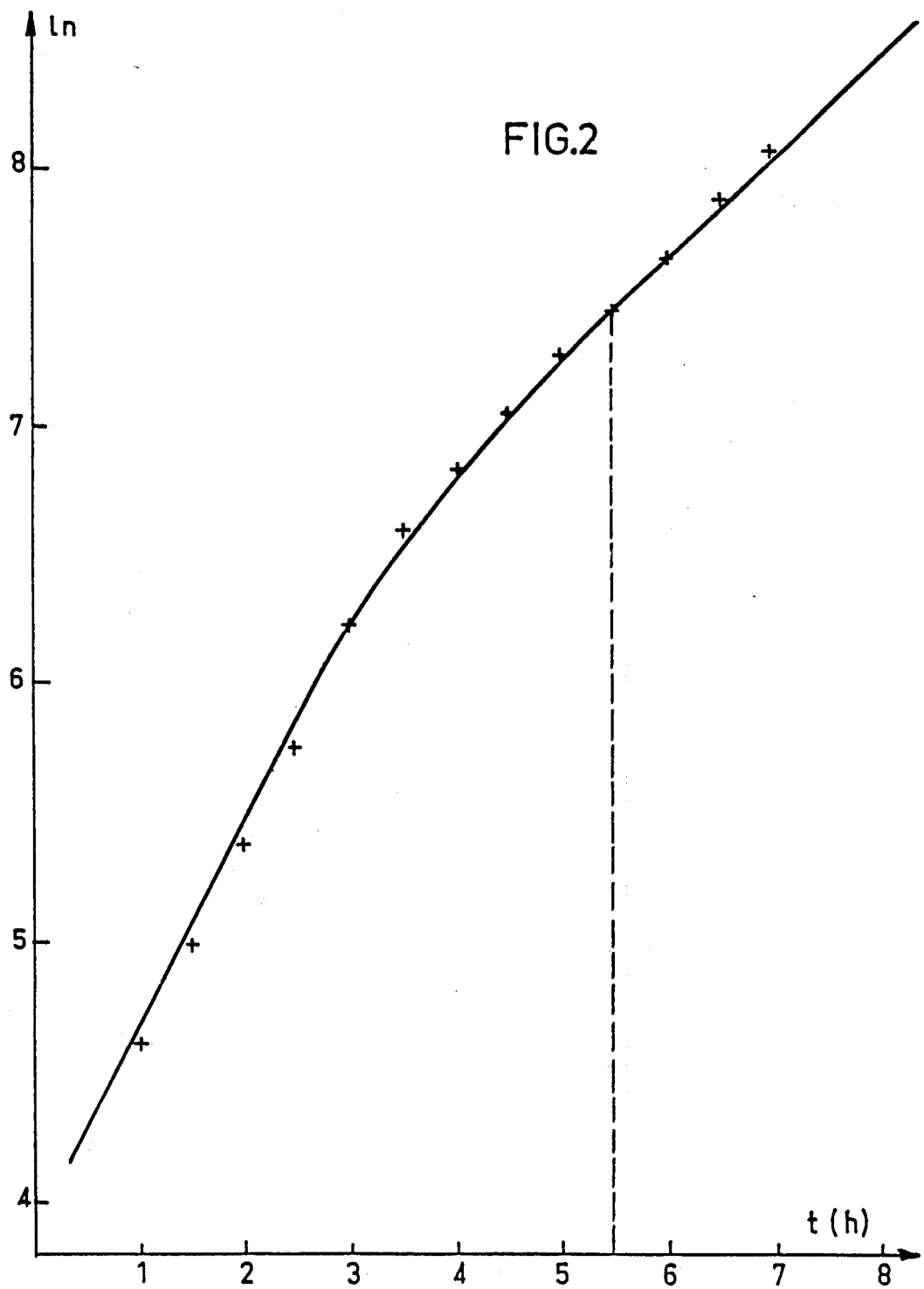
FIGS. 2 to 5 are graphs for determining the growth rate of this lactic bacteria.

A brief examination will now be made of FIGS. 2 to 5 which are graphs showing the growth rate as a function of time:

In FIG. 2, applicable to the strain CNRZ 269, a high growth rate of the order of 0.77/hr is observed during the first three hours. After 5½ hours, the concentration of lactate reaches 30 g/liter and from this instant onwards, the water supply was modified by increasing it by approximately 50%, which had the effect of reducing the ammonia concentration, thus assuring an ammonia feed into the fermenter capable of maintaining this lactate concentration at 30 g/liter which corresponds to a growth rate of 0.39/hr between 5½ and 8 hours. It will be noted that ultrafiltration is brought into operation after approximately 4 hours. At the end of the fermentation, the bacterial concentration yielded up to 32 g of dried bacteria per kg of culture. The substratum efficiency factor amounts to 7.5 kgs of lactose per kg of dried bacteria.

Figure 3:
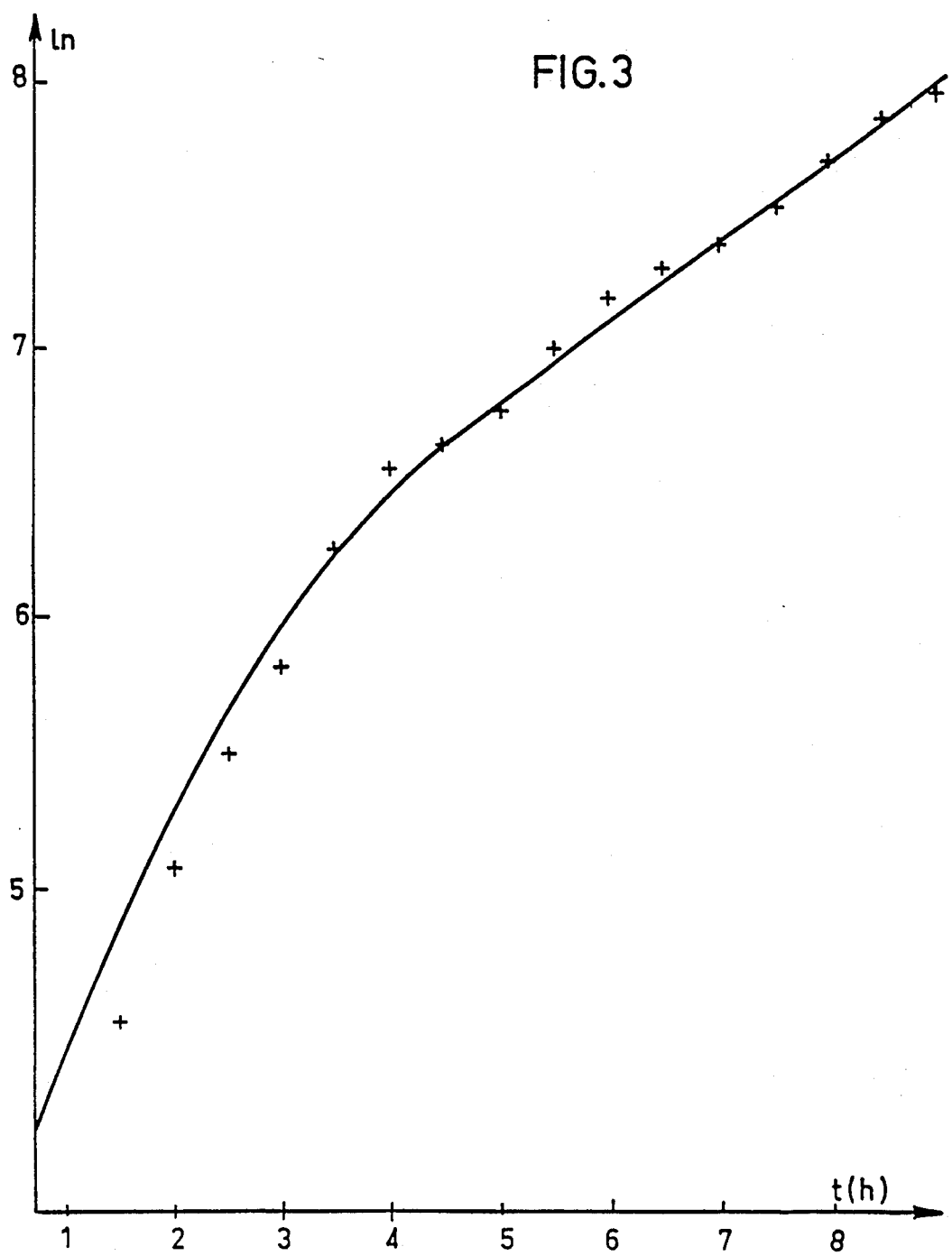

In FIG. 3, relating to strain CNRZ 116, a high growth rate of the order of 0.71/hr is observed during the first four hours. After five hours, the concentration of lactate had reached 24 g/liter, and starting from this instant, the water supply was varied by increasing it by 98%, with the result of reducing the ammonia concentration, thus assuring an infeed of ammonia into the fermenter capable of maintaining this lactate concentration at 24 g/liter which corresponds to a growth rate of 0.30/hr between 5 hours and 9 hours. It will be observed that ultrafiltration is begun a little before the end of five hours. The flow of substratum was increased by 7% before the seventh hour. At the end of the fermentation, the bacterial concentration yields 20 g of dried bacteria per kg of culture. The substratum yield factor amounts to 8.4 kgs of lactose per kg of dried bacteria.

Figure 4:
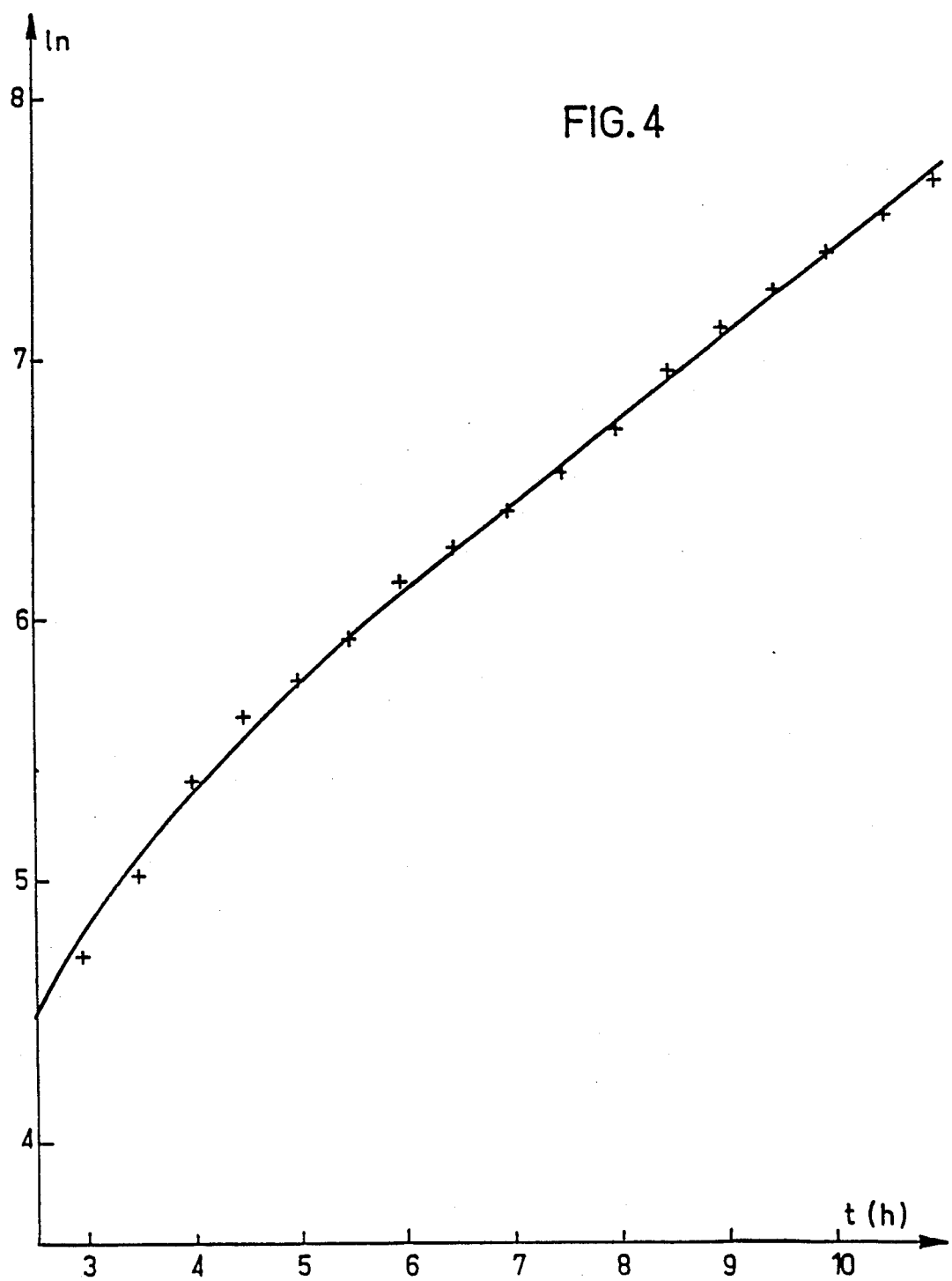

In FIG. 4, relating to strain NCDO 1119, a high growth rate of the order of 0.70/hr is observed during the first four hours. At the sixth hour, the concentration of lactate had reached 28 g/liter and starting from this instant, the water supply was varied by increasing it by 66%, which results in reducing the ammonia concentration, thus assuring an infeed of ammonia into the fermenter capable of maintaining this lactate concentration at 28 g/liter, which corresponds to a growth rate of 0.32/hr from the sixth hour to the eleventh hour. At the end of the fermentation, the bacterial concentration yields 26 g of dried bacteria per kg of culture. The substratum yield factor amounts to 9.2 kgs of lactose per kg of dried bacteria.

Figure 5:
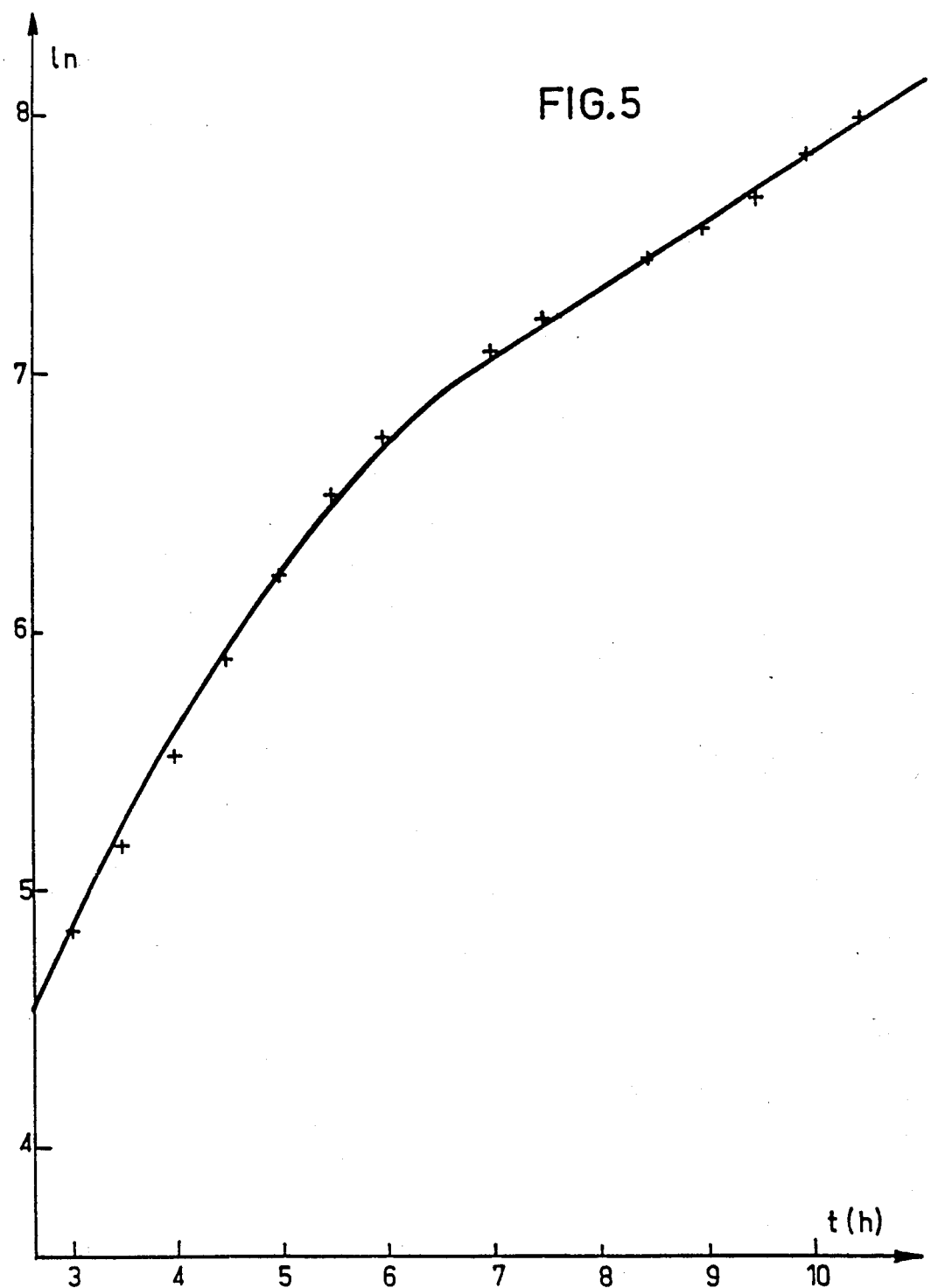

In FIG. 5 relating to strain CNRZ 125, a high growth rate of the order of 0.80/hr is observed during the first 5 hours. A little prior to the eighth hour, the concentration of lactate had reached 32 g/liter, and the water supply was varied from this instant by increasing it by approximately 42% which had the result of reducing the ammonia concentration, thus assuring a feed of ammonia into the fermenter, capable of maintaining this lactate concentration at 32 g/liter which corresponds to a growth rate of 0.26/hr from the eighth hour to the twelfth hour. It will be noted that ultrafiltration is brought into operation before the seventh hour. At the end of the fermentation, the bacterial concentration yields 18 g of dried bacteria per kg of culture. The substratum yield factor amounts to 7.9 kgs of lactose per kg of dried bacteria.

The invention is applicable for the production of microorganisms and more particularly of lactic bacteria, irrespective of their utilization, but particularly in the cheese industry, wine making industry, and so on.

What is claimed is:

1. In a process for the culturing of microorganisms in which an initially seeded growth medium is supplied with nutrient substratum, a neutralizing agent added to the growth medium and microorganism growth inhibiting agents removed by ultrafiltraton, the improvement comprising the steps of:
    initially conducting the culturing of microorganisms in said medium in a fermentation zone during a first stage in the absence of ultrafiltration while maintaining the pH of said growth medium at a value within the range of 6-7 by the addition of a neutralizing agent;
    adding nutrient substratum and dilution water to the growth medium during said first stage in an amount sufficient to maintain the growth rate of the microorganisms at a constant predetermined level, the amount of nutrient substratum and dilution water added being maintained at constant proportions relative to the amount of neutralizing agent added during said first stage, the volume of said growth medium being permitted to increase as a result of the additions;
    conducting the culturing of said microorganisms in said medium during a second stage in said fermentation zone while maintaining the growth rate less than the growth rate in the first stage and in the range of 0.10 to 0.50/hr by increasing the amount of dilution water added relative to the amounts of nutrient substratum and neutralizing agent added, the amount of dilution water added being sufficient to maintain the concentration of growth inhibiting agents present in said growth medium at a constant predetermined maximum level so as to achieve the desired growth rate;
    continuously removing growth inhibiting agents by ultrafiltration from said growth medium in said fermantation zone during said second stage while maintaining a substantially constant volume of said growth medium in said fermentation zone; and
    ceasing said first stage and initiating said second stage of culturing in said fermentation zone upon the amount of growth inhibiting agents present in said growth medium during said first stage reaching said predetermined maximum level.

2. A process as claimed in claim 1, wherein said growth rate in said second stage ranges from 0.15/hr. to 0.45/hr.

3. A process according to claim 1, wherein said growth rate in said second stage ranges from 0.20/hr to 0.40/hr.

4. A process according to claim 1, wherein said growth rate in said second stage ranges from 0.30/hr to 0.35/hr.

5. A process according to claim 1, wherein the nutrient substratum is added in an amount sufficient to maintain the nutrient substratum concentration at a constant level during both said first and second stages.

6. A process according to claim 1, wherein said growth rate in said first stage ranges from 0.70/hr to 0.80/hr.

7. A process according to claim 1, wherein said nutrient substratum comprises lactose and yeast extract.

8. A process according to claim 7, wherein during said second stage, the lactose concentration in the growth medium ranges from 50 g/l for a growth rate of 0.10/hr to 18 g/l for a growth rate of 0.5/hr, the yeast extract concentration ranges from 8 g/l for a growth rate of 0.10/dr to 18 g/l for a growth rate of 0.5/hr, and wherein the neutralizing agent is ammonia and the ammonia concentration ranges from 0.50N for growth rate of 0.10/hr to 0.18N for growth rate of 0.50/hr.

9. A process as claimed in claim 1, wherein the addition of nutrient substratum, dilution water and neutralizing agent in said first stage is automatically controlled.

10. A process as claimed in claim 1, wherein the volume of the growth medium is permitted to increase during said first stage, said volume being permitted to decrease during said second stage and subsequently maintained at said constant volume.

11. A process as claimed in claim 1, wherein said neutralizing agent is selected from the group consisting of ammonia and soda.

* * * * *